US008226971B2

(12) United States Patent
Ash et al.

(10) Patent No.: US 8,226,971 B2
(45) Date of Patent: Jul. 24, 2012

(54) CATHETER LOCK SOLUTION COMPRISING CITRATE AND A PARABEN

(75) Inventors: Stephen R. Ash, Lafayette, IN (US); Janusz Steczko, West Lafayette, IN (US); Gary L. Swanson, Elkhorn, WI (US)

(73) Assignee: Ash Access Technology, Inc., West Lafayette, IN (US)

( * ) Notice: Subject to any disclaimer, the term of this patent is extended or adjusted under 35 U.S.C. 154(b) by 87 days.

(21) Appl. No.: 12/792,286

(22) Filed: Jun. 2, 2010

(65) Prior Publication Data

US 2010/0240750 A1 Sep. 23, 2010

Related U.S. Application Data

(62) Division of application No. 11/053,130, filed on Feb. 8, 2005, now Pat. No. 7,749,529.

(51) Int. Cl.
*A01N 37/10* (2006.01)
(52) U.S. Cl. .......................... 424/423; 514/544
(58) Field of Classification Search .................. None
See application file for complete search history.

(56) References Cited

U.S. PATENT DOCUMENTS

| | | | |
|---|---|---|---|
| 4,187,719 A | 2/1980 | Brethauer |
| 4,193,980 A | 3/1980 | Clason et al. |
| 4,225,254 A | 9/1980 | Holberg et al. |
| 4,225,669 A | 9/1980 | Melnick et al. |
| 4,364,929 A | 12/1982 | Sasmor et al. |
| 4,677,143 A | 6/1987 | Laurin et al. |
| 4,853,227 A | 8/1989 | Kurihara-Bergstrom et al. |
| 4,885,855 A | 12/1989 | Marks, Sr. et al. |
| 4,929,242 A | 5/1990 | Desecki et al. |
| 4,950,665 A | 8/1990 | Floyd |
| 4,973,328 A | 11/1990 | Smith |
| 4,980,374 A | 12/1990 | Steudle et al. |
| 5,002,965 A | 3/1991 | Ramwell et al. |
| 5,032,615 A | 7/1991 | Ward et al. |
| 5,043,357 A | 8/1991 | Hoffler et al. |
| 5,088,996 A | 2/1992 | Kopfer et al. |
| 5,103,817 A | 4/1992 | Reisdorf et al. |
| 5,109,025 A | 4/1992 | Satoh et al. |
| 5,436,007 A | 7/1995 | Hartung et al. |
| 5,571,666 A | 11/1996 | Floyd et al. |
| 5,647,855 A | 7/1997 | Trooskin |
| 5,665,061 A | 9/1997 | Antwiler |
| 5,688,516 A | 11/1997 | Raad et al. |
| 5,709,672 A | 1/1998 | Illner |
| 5,709,993 A | 1/1998 | Buturovic-Ponikvar |
| 5,811,471 A | 9/1998 | Shanbrom |
| 5,827,244 A | 10/1998 | Boettger |
| 5,843,016 A | 12/1998 | Lugnani et al. |
| 5,858,641 A | 1/1999 | Shanbrom |
| 5,902,283 A | 5/1999 | Darouiche et al. |
| 6,022,551 A | 2/2000 | Jampani et al. |
| 6,025,312 A | 2/2000 | Saito et al. |
| 6,034,133 A | 3/2000 | Hendley et al. |
| 6,080,417 A | 6/2000 | Kramer et al. |
| 6,166,007 A | 12/2000 | Sodemann |
| 6,183,764 B1 | 2/2001 | Shanbrom |
| 6,187,768 B1 | 2/2001 | Welle et al. |
| 6,190,371 B1 | 2/2001 | Maginot et al. |
| 6,207,107 B1 | 3/2001 | Debrauwere et al. |
| 6,239,048 B1 | 5/2001 | Wilson et al. |
| 6,258,797 B1 | 7/2001 | Lehner |
| 6,346,529 B1 | 2/2002 | Floyd et al. |
| 6,350,251 B1 | 2/2002 | Prosl et al. |
| 6,361,524 B1 | 3/2002 | Odell et al. |
| 6,361,786 B1 | 3/2002 | Shanbrom |
| 6,423,050 B1 | 7/2002 | Twardowski |
| 6,423,329 B1 | 7/2002 | Sine et al. |
| 6,423,706 B2 | 7/2002 | Sodemann |
| 6,451,003 B1 | 9/2002 | Prosl et al. |
| 6,488,665 B1 | 12/2002 | Severin et al. |
| 6,498,157 B2 | 12/2002 | Sodemann |
| 6,566,402 B2 | 5/2003 | Warnock |
| 6,569,852 B1 | 5/2003 | Sodemann |
| 6,592,564 B2 | 7/2003 | Finch et al. |
| 6,679,870 B1 | 1/2004 | Finch et al. |
| 6,685,694 B2 | 2/2004 | Finch et al. |
| 6,723,350 B2 | 4/2004 | Burrell et al. |
| 6,743,216 B2 | 6/2004 | Odell et al. |

(Continued)

FOREIGN PATENT DOCUMENTS

CN 1448051 A 10/2003

(Continued)

OTHER PUBLICATIONS

TRICITRASOL, product description, Cytosol Labratories, Jun. 2003.*
Shah et al. (Antimicrobial Agents and Chemotherapy, 2000).*
U.S. Appl. No. 60/364,335, filed Mar. 14, 2002, Ash et al.
Adams et al., *J. Hosp. Infection*, 61, 287-290 (2005).
Ash et al., "Concentrated sodium citrate as catheter lock solution," *J. Am. Soc. Nephrol.* 10:272A (Sep. 1999).
Ash et al., "Concentrated Sodium Citrate (23%) as Catheter Lock Solution," *ASN Program and Abstracts 32nd Annual Meeting and 1999 Renal Week*, Miami Beach, FL (Nov. 1-8, 1999).
Ash et al., "Concentrated Sodium Citrate (23%) for Catheter Lock," *Hemodial Int.*, vol. 4, pp. 22-31 (2000).
Bell et al, "Ethanol/trisodium citrate for hemodialysis catheter lock," *Clin. Nephrology*, 62 (5), 369-373 (Nov. 2004).
Bleasdale et al., "Effectiveness of chlorhexidine bathing to reduce catheter-associated bloodstream infections in medical intensive care unit patients," *Arch. Intern. Med.*, 167 (19), 2073-2079 (Oct. 22, 2007).
Branson et al., "Efficacy of 1.4 percent sodium citrate in maintaining arterial catheter patency in patients in a medical ICU," *Chest*, vol. 103, No. 3, pp. 882-885 (Mar. 1993).

(Continued)

*Primary Examiner* — Robert A Wax
*Assistant Examiner* — Danah Al-Awadi
(74) *Attorney, Agent, or Firm* — Leydig Voit & Mayer, Ltd.

(57) ABSTRACT

This invention relates to compositions, methods, devices and kits relating to the infusion of a catheter lock solution into an indwelling catheter. Inventive compositions, methods, devices and kits aid in diminishing the effects of microbial infection in catheters and occlusion of the catheters. A lock solution provided by the invention includes citrate and a paraben. The solution preferably has a density suitable for retention of the solution in a catheter during the lock period. Another lock solution provided by the invention includes citrate, a paraben and a photo-oxidant, such as, for example, methylene blue.

24 Claims, 1 Drawing Sheet

U.S. PATENT DOCUMENTS

| | | | |
|---|---|---|---|
| 6,881,731 | B1 | 4/2005 | Shanbrom |
| 6,958,049 | B1 | 10/2005 | Ash |
| 6,962,714 | B2 | 11/2005 | Hei et al. |
| 7,422,388 | B2 | 9/2008 | Tufts et al. |
| 7,601,731 | B2 * | 10/2009 | Raad .......................... 514/279 |
| 7,749,529 | B2 | 7/2010 | Ash et al. |
| 2002/0165278 | A1 | 11/2002 | Konowalchuk et al. |
| 2002/0182265 | A1 | 12/2002 | Burrell et al. |
| 2003/0078242 | A1 | 4/2003 | Raad et al. |
| 2003/0212443 | A1 | 11/2003 | LaMuraglia |
| 2004/0092890 | A1 | 5/2004 | Ash |
| 2004/0219179 | A1 | 11/2004 | McDaniel |
| 2004/0225265 | A1 | 11/2004 | Tapadiya |
| 2005/0013836 | A1 | 1/2005 | Raad |
| 2005/0084471 | A1 | 4/2005 | Andrews et al. |
| 2005/0131356 | A1 | 6/2005 | Ash et al. |
| 2005/0177887 | A1 | 8/2005 | Melmed et al. |
| 2005/0197364 | A1 | 9/2005 | Kelly et al. |
| 2005/0215978 | A1 | 9/2005 | Ash |
| 2006/0177477 | A1 | 8/2006 | Ash et al. |
| 2006/0204466 | A1 | 9/2006 | Littau et al. |
| 2006/0204467 | A1 | 9/2006 | Littau et al. |
| 2006/0264423 | A1 | 11/2006 | Wood et al. |
| 2007/0012713 | A1 | 1/2007 | Wentworth et al. |
| 2007/0105848 | A1 | 5/2007 | Wood et al. |
| 2007/0112062 | A1 | 5/2007 | Luengo et al. |
| 2007/0184016 | A1 | 8/2007 | Macinga et al. |
| 2007/0225662 | A1 | 9/2007 | Rucinski |
| 2007/0231051 | A1 | 10/2007 | Flores et al. |
| 2007/0241306 | A1 | 10/2007 | Wehner et al. |
| 2008/0279907 | A1 | 11/2008 | Ash et al. |
| 2009/0291944 | A1 | 11/2009 | Ash et al. |

FOREIGN PATENT DOCUMENTS

| | | |
|---|---|---|
| JP | H04-502324 A | 4/1992 |
| WO | WO 90/06759 A1 | 6/1990 |
| WO | WO 00/01391 A1 | 1/2000 |
| WO | WO/00/10385 * | 3/2000 |
| WO | WO 00/10385 A1 | 3/2000 |
| WO | WO/01/85249 * | 11/2001 |
| WO | WO 01/85249 A1 | 11/2001 |
| WO | WO 2008/019083 | 2/2008 |

OTHER PUBLICATIONS

Bredin et al., "Propyl paraben induces potassium efflux in *Escherichia coli*," *J. Antimicrob. Chemother.*, 55, 1013-1015 (2005).

Brown et al., "Can alcohol-based hand-rub solutions cause you to lose your driver's license? Comparative cutaneous absorption of various alcohols" *Antimicrobial Agents and Chemotherapy*, 51 (3), 1107-1108 (Mar. 2007).

Buturovic et al., Filling hemodialysis catheters in the interdialytic period; heparin versus citrate versus polygeline: a prospective randomized study; *Artificial Organs*, vol. 22, No. 11, pp. 945-947 (Nov. 1998).

Carratala et al., "Randomized, Double-blind Trial of an Antibiotic-lock Technique for Prevention of Grain-positive Central Venous Catheter-related Infection in Neutropenic Patients with Cancer," *Antimicrobial Agents and Chemotherapy*, vol. 43, No. 9, pp. 2200-2204 (1999).

Declaration of Dr. Kees Baggerman, submitted in proceedings of Opposition re: European Patent No. 1107807, 1 pp (May 4, 2009).

Demidova et al., "Photodynamic inactivation of *Bacillus* spores, mediated by phenothiazinium dyes," *Applied and Environmental Microbiology*, 71 (11), 6918-6925 (2005).

Denyer, "Mechanisms of action of antibacterial biocides," *Int'l Biodeterioration and Biodegradation*, 36, 227-245 (1995).

Doron et al., "Antibacterial effect of parabens against planktonic and biofilm *Streptococcus sobrinus*," *Int. J. Antimicrob. Agents*, 18, 575-578 (2001).

Dzik et al., Citrate toxicity during massive blood transfusion; *Transfusion Medicine Reviews*, vol. 2, No. 2, pp. 76-94 (Jun. 1988).

Edmiston et al., "Comparative of a new and innovative 2% chlorhexidine gluconate-impregnated cloth with 4% chlorhexidine gluconate as topical antiseptic for preparation of the skin prior to surgery," *Am. J. Infect. Control*, 35 (2), 89-96 (Mar. 2007).

Elliot et al., "Preoperative Skin Preparation for Minimally Invasive Surgery," *Supplement to VDM*, 3-6 (Mar./Apr. 2008).

European Pharmacopoeia, 6.0, pp. 1200-1203 (2007).

Flanigan et al., "Regional Hemodialysis anticoagulation: hypertonic tri-sodium citrate or anticoagulant citrate dextrose-A" *Am J Kidney Dis*, vol. 27, pp. 519-524 (Apr. 1996).

Georgopoulou et al., "Evaluation of the antimicrobial effectiveness of citric acid and sodium hypochlorite on the anaerobic flora of the infected root canal," *International Endodontic Journal*, 27: 139-143 (1994).

Hesse et al., Experimental investigations on dissolution of incrustations on the surface of catheters, *Urologia Internationalis*, vol. 44, No. 6, pp. 364-369 (1989).

Hesse et al., In vitro investigations into the formation and dissolution of infection-induced catheter encrustations, *British Journal of Urology*, vol. 70. No. 4, pp. 429-434 (Oct. 1992).

Hibbard et al., "A clinical study comparing the skin antisepsis and safety of ChloraPrep, 70% isopropyl alcohol, and 2% aqueous chlorhexidine," *J. Infusion Nursing*, 25 (4), 244-249 (Jul./Aug. 2002).

Hibbard, "Analyses comparing the antimicrobial activity and safety of current antiseptic agents: a review," *J. Infusion Nursing*, 28 (3), 194-207 (May/Jun. 2005).

Interlocutory Decision in Opposition re: European Patent No. 1107807, 31 pp (Jan. 5, 2009).

IUPAC Compendium of Chemical Terminology, "IUPAC Nomenclature of Inorganic Chemistry," Third Edition, Blackwell Scientific Publications, http://goldbook.iupac.org/S05447.html and http:goldbook.iupac.org/src R.B..html, submitted in proceedings of Opposition re: European Patent No. 1107807 on Aug. 14, 2007, 1 pp.

Kampf et al., "Limited effectiveness of chlorhexidine based hand disinfectants against methicillin-resistant *Staphylococcus aureus* (MRSA)," *J. Hosp. Infection*, 38, 297-303 (1998).

Kelleher et al., Severe metabolic alkalosis complicating regional citrate hemodialysis; *Am J Kidney Dis*, vol. 9, No. 3, pp. 235-236 (1987).

Kristiansen et al., "The potential management of resistant infections with non-antibiotics," *J. Antimicrob. Chemo.*, 40, 319-327 (1997).

Leray-Moragues et al., "Gentamicin/sodium citrate mixture: a promising antibiotic lock for preventing catheter related infections," Lepeyronie University Hospital, Montpellier, France (Date Unknown).

Leray-Moragues et al., Antibiotic Lock, an Effective Manner for Preventing Permanent Catheter Related Infections (Date Unknown).

Levin et al., "The Use of Heated Citric Acid for Dialyzer Reprocessing," *Journal of the American Society of Nephrology*, 6(6); 1578-1585 (1995).

Lide (Ed.), "The CRC Handbook of Chemistry and Physics," $84^{th}$ Edition, p. 2-55 (2003-2004).

Lim et al., "Infection prevention for cardiac catheterization and minimally invasive procedures," *Supplement to VDM*, 7-9 (Mar./Apr. 2008).

Lohr et al., Safety of regional citrate hemodialysis in acute renal failure; *Am J of Kidney Dis*, vol. 13, No. 2, pp. 104-107 (Feb. 1989).

Ma et al., "Irreversible paraben inhibition of glycolysis by *Streptococcus mutans* GS-5," *Lett. Appl. Microbiol.*, 23, 329-333 (1996).

Mimoz et al., "Chlorhexidine-based antiseptic solution vs alcohol-based povidone-iodine for central venous catheter care," *Arch. Intern. Med.*, 167(19), 2066-2072 (Oct. 22, 2007).

Minutes of Oral Proceeding re: European Patent No. 1107807, 13 pp (Nov. 27, 2008).

Nes et al., "The effect of parabens on DNA, RNA, and protein synthesis in *Escherichia coli* and *Bacillus subtilis*," *J. Appl. Bacteriology*, 54, 237-242 (1983).

Nguyen et al., "The effects of parabens on the mechanosensitive channels of *E. coli*," *Eur. Biophs. J.*, 34 (5), 389-395 (Jul. 2005).

Notice of Opposition and Annexes re: European Patent No. 1107807, 17 pp., Aug. 14, 2007.

Olinger et al., Acute clinical hypocalcemic myocardial depression during rapid blood transfusion and postoperative hemodialysis; *Journal of Thoracic and Cardiovascular Surgery*, vol. 72, No. 4, pp. 503-511 (Oct. 1976).

Onder et al., "Controlling exit site infections: does it decrease the incidence of catheter-related bacteremia in children on chronic hemodialysis?" *Hemodialysis Int'l.*, 13, 11-18 (Jan. 2009).

Oxford et al., "Inactivation of Influenza and Other Viruses by a Mixture of Virucidal Compounds," *Applied Microbiology*, 21(4): 606-610 (1971).

Percival et al., "Assessing the effect of an antimicrobial wound dressing on biofilms," *Wound Repair Regen*, 16, 52-57 (2008).

Polaschegg HD, "Taurolidine, a new antimicrobial catheter lock solution," Renal Research Institute, *Dialysis Times*, vol. 7, No. 2 (Jun. 2000).

Poli et al., "Virucidal Activity of Organic Acids," *Food Chemistry*, 4: 251-258 (1979).

Purchase et al., Hemodialysis with a permcath kept open with streptokinase and later citrate in a heparin-sensitive patient; *Nephron*, vol. 58, pp. 119-120 (1991).

Response to Grounds for Appeal re: European Patent No. 1107807, 37 pp (Nov. 30, 2009).

Response to Opposition re: European Patent No. 1107807, 27 pages (Mar. 10, 2008).

Rice et al., "Effect of increasing methylation on the ability of methylene blue to cause diaphorase-catalysed oxidation of NADH," *Biochem. Soc. Trans.*, 26, S319 (1998).

Roberts, "Value of methylene blue-gentian violet 5 per cent in preoperative skin preparation," *Annals of Surgery*, 89 (2), 183-190 (Feb. 1929).

Rosen et al., "Lower Gastrointestinal Bleeding: Approach to Lower GI Bleeding," *ACS Surgery Online*, WedMD Inc., NewYork—posted Jun. 7, 2006 (http://www.medscape.com/viewarticle/535552) 7 pgs.

Russell et al., *Int'l J. Pharmaceutics*, 34, 115-123 (1986).

Shah, et al., Antimicrobial Activity of a Novel Catheter Lock Solution; *Antimicrobial Agents and Chemotherapy*, 1674-1679; vol. 46, No. 6, American Society for Microbiology (Jun. 2002).

Shanks et al., "Catheter lock solutions influence staphylococcal biofilm formation on abiotic surfaces," *Nephrol. Dial. Transplant*, 21, 2247-2255 (Apr. 2006).

Sodemann et al., Gentamicin/sodium-citrate mixture as antibiotic-lock technique for salvage and prevention of catheter-related infections—A four year trial; *J am Soc Nephrol*, vol. 8, p. 173A (1997).

Sodemann et al., Prevention of Sepsis in HD Patients with Catheters using an Antimicrobial Lock; *J. Am. Soc. Nephrol.* 12: A1559 (2001).

Statement of Grounds for Appeal re: European Patent No. 1107807, 25 pp (May 4, 2009).

Steczko et al., "Microbial inactivation properties of a new antimicrobial/antithrombotic catheter lock solution (citrate/methylene blue/parabens)," *Nephrol Dial Transplant*, No. 24, pp. 1937-1945 (2009).

Steczko et al., "In vitro and in vivo evaluation of efficacy of citrate/methylene blue/parabens/IPA solution as a skin disinfectant," *J. Infection*, 60, 36-43 (2010).

Summons to Oral Proceedings re: European Patent No. 1107807, 8 pages (Jun. 10, 2008).

Submission of Auxiliary Requests and Data re: European Patent No. 1107807, 28 pages (Oct. 27, 2008).

Tu et al., "Heparin-free hemodialysis with citrate-containing dialysate in intensive care patients," *Dialysis and Transplantation*, vol. 29, No. 10, pp. 620-624 (Oct. 2000).

TRICITRASOL, product description, Cytosol Labratories (Jun. 2003).

Usacheva et al., "Comparison of the methylene blue and toluidine blue photobactericidal efficacy against gram-positive and gram-negative microorganisms," *Lasers in Surgery and Medicine*, 29, 165-173 (2001).

Usacheva et al., "The interaction of lipopolysaccharides with phenothiazine dyes," *Lasers in Surgery and Med.*, 33, 311-319 (2003).

VanHolder et al., "Influence of uraemia and haemodialysis on host defense and infection," *Nephrology Dial Transplant*, 11: 593-598 (1996).

Von Brecht et al., Regional anticoagulation: hemodialysis with hypertonic trisodium citrate; *Am J of Kidney Dis*, vol. 8, No. 3, pp. 196-201 (Sep. 1986).

Wainwright et al., "A study of photobactericidal activity in the phenothiazinium series," *FEMS Immunology and Medical Microbiology*, 19, 75-80 (1997).

Wainwright et al., "Photobacterial Activity of Phenothiazimium Dyes Against Methicilin-resistant Strains of *Staphylococcus aureus*," *FEMS Miscrobiology Letters*, No. 160, pp. 177-181 (1998).

Wainwright et al., "Photobactericidal activity of methylene blue derivatives against vancomycin-resistant *Enterococcus* spp," *J. Antimicrob. Chemother.*, 44, 823-825 (1999).

Wainwright et al., "Methylene Blue—a therapeutic dye for all seasons?" *J. Chemother.*, 14 (5), 431-443 (Oct. 2002).

Weast (Ed.), "The CRC Handbook of Chemistry and Physics," 57$^{th}$ Edition, p. F-118 (1976-1977).

Weijmer et al., "Superior Antimicrobial Activity of Trisodium Citrate Over Heparin for Catheter Locking," *Nephrol. Dial. Transplant*, No. 17, pp. 2189-2195 (2002).

Yamaguchi et al., "Root Canal Irrigation with Citric Acid Solution," *Journal of Endodontics*, 22(1): 27-29 (1996).

Zuragen Clinical Trial, "A Multi-Centered, Two-Arm, Randomized Study Comparing the Effects of AAT-023 (Zuragen) Solution, and Heparin on the Incidence of Catheter Related Blood Stream Infections in Tunneled chronic Central Venous Catheters for Dialysis," ClinicalTrials.gov, 5 pgs. (2008) (http://clinicaltrials.gov/ct2/show/NCT00628680?term=zuragen&rank=1).

* cited by examiner

CATHETER LOCK SOLUTION COMPRISING CITRATE AND A PARABEN

BACKGROUND

This invention generally relates to catheters and methods of preventing occlusion and infection of catheters, such as intravascular catheters and other body cavity catheters. More specifically, but not exclusively, this invention relates to infusing a lock solution into an indwelling catheter, such as, for example, an indwelling intravascular catheter, for inhibiting occlusion and infection in an animal having an indwelling catheter.

By way of background, catheters are used with increasing frequency to treat patients requiring a variety of medical procedures. Catheters offer many advantages for patients; for example, catheters provide ready access to a patient's vasculature without repeated injections for infusion of fluids such as drugs, nutrients, electrolytes or fluids used in chemotherapy, or for the removal of blood on an intermittent basis. In hyperalimentation treatment, catheters are usually used for infusion of large volumes of fluids. In chemotherapy, catheters are used for infusion of drugs on an intermittent basis, ranging from daily to weekly. For hemodialysis, dual-lumen catheters are typically used—usually three times per week— to remove blood from the patient's circulatory system for treatment and to return treated blood back to the patient. One lumen allows removal of blood, while the other lumen allows blood to return.

Catheters are also used to perform other functions and to convey fluids into and out of other body cavities besides veins, as noted above. For example, catheters are placed into arteries to measure blood pressure or remove arterial blood for analysis of gases reflecting lung function; catheters are placed into the peritoneum (the space surrounded by the peritoneal membrane and external to organs in the abdomen) to perform peritoneal dialysis and remove fluids and toxins from the patient; and other catheters are placed into the fluid around the nervous system (cerebral spinal fluid) for removal of this fluid or administration of drugs, and into the subcutaneous space for administration of various drugs or fluids. Such catheters are also subject to infection and to other problems addressed herein.

Catheters can either be acute, or temporary, for short-term use or chronic for long-term treatment. Catheters used to access a patient's bloodstream are commonly inserted into central veins (such as the vena cava) from peripheral vein sites. Another alternative is placement of a dual-lumen chronic central venous dialysis catheter (a "CVDC") through the internal jugular vein. Adequate hemodialysis requires removal and return of 250-400 mL of blood per minute.

Catheters, especially chronic venous catheters, have drawbacks. The use of both temporary and chronic CVDCs is associated with certain complications that may require catheter removal, catheter replacement and/or administration of medical therapies. They can become occluded by a thrombus, and even if extreme care is taken, the catheters can increase a patient's risk of infection.

Considering first the problem of infection, great care must be taken in the placement and use of a chronic catheter to prevent infection of the patient at the site of access or within the vascular system. The foreign surfaces of catheters can create smooth surfaces at which bacteria can grow, and at which white cells are unable to surround or "phagocytize" the bacteria. One way that a catheter, particularly a chronic catheter such as a CVDC, can give rise to infection is by the migration of bacteria around the catheter across the protective dermal layers. To address this problem, a chronic CVDC usually includes a DACRON cuff attached to the catheter and placed under the skin, which promotes ingrowth of fibrous tissue, fixes the catheter in position, and prevents bacterial migration around the catheter. Most chronic CVDCs in use in the U.S. today have single subcutaneous Dacron® cuffs, placed in the tunnel, 1-4 cm beneath the skin exit site. For dual lumen catheters such as the Ash Split Cath™ and Bard Hickman® catheters, there is one cuff on the catheter. For single-lumen catheters such as Tesio® catheters, there is a single Dacron cuff for each catheter. Cuffed, tunneled CVDCs have a decrease in the rate of exit site infection and catheter-related bloodstream infection ("CRBSI") versus uncuffed catheters, but these infections still occur. It is believed that the only chronic CVDC in the U.S. at present that does not have a subcutaneous Dacron cuff is the Schon™ catheter. In this catheter a subcutaneous plastic clip connects two Tesio catheters. This clip fixes the catheters in position and apparently prevents pericatheter bacterial migration in a manner similar to a Dacron cuff. Chronic CVDCs are typically made from one of three types of materials: silicone, polyurethane, or polyurethane derivatives.

For chronic CVDC the most common cause of catheter infection is contamination of the connector hub, and the predominant route of contamination is endoluminal. Catheters, particularly venous catheters, are frequently accessed with syringes, or uncapped and directly connected to IV lines, creating a situation wherein the probability of microbial infection is relatively high. The major determinant of the rate of infection is the frequency with which the catheter hub is opened and the major preventive step is the care in disinfection of the hub and prevention of contamination of the hub. Since endoluminal contamination is the major cause of CRBSI in chronic CVDC, the determinants of infection center on the procedures and handling of the catheter.

Several studies have indicated a rate of bloodstream infection during use of chronic CVDC of 1.1 to 2.2 per 1,000 patient days. One study demonstrated a catheter-related bacteremia rate of 2.2 to 3.8 bacteremic episodes per 1,000 patient days, the lower rate being for catheters placed surgically rather than radiologically. Another study of new tunneled catheters reported that 19% of catheters became infected in a mean of 62 days after catheter placement, representing a rate of 3 infections per 1,000 days. This means that each patient has approximately a 10% chance of developing bloodstream infection during each month. There is no evidence that the rate of CRBSI increases with duration of use of a chronic CVDC. In fact, practical experience and various studies have shown that the rate of CRBSI is the same over the many months of use. Tests indicate that the risk of CRBSI is the same for each period of time that the patient has a catheter. Over time the patient has a higher chance for infection merely because there is more time at risk for infection. The longer the patients have a chronic CVDC, the greater the chance that an infection will occur, but this is merely due to greater time for a constant risk of exposure.

CRBSI in dialysis patients is usually associated with modest symptoms and clears after antibiotic therapy. However, in some patients, signs of infection are much more severe and include all of the symptoms of Systemic Inflammatory Response Syndrome ("SIRS") (tachycardia, tachypnea, abnormal temperature and white count) plus hypotension. Often these patients must be hospitalized and given intravenous antibiotics. In spite of this care, patients often remain seriously ill until the infected catheter is removed. Studies have shown that CRBSI in hemodialysis patients is caused most frequently by *Staphylococcus* species such as *S. Epider-*

*midis*. However, hemodialysis patients are reported to have a greater proportion of CRBSIs due to *S. Aureus* than do other patient populations and a significant number of infections are due to gram-negative organisms.

The mortality rate following CRBSI in ICU patients has been reported to be 3-25%. It was reported in a recent year that about 60,000 of the 300,000 patients on dialysis in the U.S. had chronic CVDC. Assuming an average incidence of CRBSI of only 21,000 patient-days at risk, about 120 of these patients would be expected to develop CRBSI each day. At the lowest reported mortality rate of 3%, 3-4 ESRD patients die from CRBSI each day. At the highest reported mortality of 25%, 30 ESRD patients die from CRBSI each day. Furthermore, the cost attributable to caring for a single CRBSI episode in hospitalized patients has been reported to be between $3,700 and $29,000. Costs may be higher for patients with CRBSI related to chronic CVDC, given the higher cost of removing and replacing a chronic CVDC. Given the serious consequences of CRBSI, the acute illness of the patient who apparently has bacteremia, and the frequent decision to remove the catheter on the presumption that it is the source, there is a great need for alternative means for fighting catheter infection.

Turning now to the problem of catheter occlusion, intraluminal thrombus formation can significantly impair catheter flow, as can thrombus formation just outside the tip of the catheter. Impairment of the flow may lead to catheter removal or administration of drugs such as tPA to resolve these thromboses. In order to prevent clotting of catheters in blood vessels between uses of a CVDC, catheters have commonly been filled with a lock solution that comprises a concentrated solution of the commonly used anticoagulant, heparin (usually up to 10,000 units of heparin per catheter lumen). The heparin lock solution is injected into each lumen immediately after each use, and typically left in the catheter until the catheter is accessed again. The heparin lock solution is then withdrawn from the catheter before the next use because infusing this amount of heparin into a patient's bloodstream runs the risk of causing excessive bleeding. During the catheter lock procedure the injected volume of solution is preferably exactly the same as the internal volume of the catheter. Even when this volume is injected exactly, however, about ⅓ of the injected anticoagulant volume typically leaves the end of the catheter, causing some systemic anticoagulation of the patient in the hours after a dialysis procedure.

Even with the use of a heparin lock solution, the catheter can become occluded between uses from coagulation of blood in the catheter. Blood may be found in the catheter because, for example, an inadequate volume of heparin was originally infused within the catheter lumen, the heparin diffused or convected from the lumen, or residual blood remains in the lumen during the catheter lock. This often results in formation of a thrombus with concomitant loss of flow through the lumen. The occluded catheters frequently must be removed and/or replaced.

Furthermore, it has been reported that thrombi and fibrin deposits on catheters may serve as a nidus for microbial colonization of the intravascular devices, and that catheter thrombosis might therefore be one factor associated with infection of long-term catheters. Thus, the use of anticoagulants or thrombolytic agents may have a role in the prevention of catheter-related bloodstream infections. However, recent in vitro studies suggest that the growth of coagulase-negative Staphylococci on catheters may also be enhanced in the presence of heparin. In addition, the routine use of heparin to maintain catheter patency, even at doses as low as 250 to 500 units per day, has caused some patients with anti-heparin antibodies to experience heparin-induced thrombocytopenia (HIT Syndrome). This serious syndrome can result in severe and sudden thromboembolic and hemorrhagic complications.

Heparin solutions have no proven intrinsic antiseptic properties to prevent infection after catheter hub contamination. The lack of antiseptic properties of a 5000 U/mL heparin lock was confirmed by a study performed by BEC Laboratories, Inc. under the standard USP antimicrobial effectiveness test protocol. "Antiseptic", as used herein, means "relating to the prevention of infection by inhibiting the growth of infectious agents", as defined in Stedman's medical dictionary. Heparin, in fact, may help to promote growth of bacteria within the "biofilm" layer of protein on the catheter surfaces (protamine has the opposite effect). The "biofilm" proteins on the catheter surfaces can protect bacteria from antibiotics and white cells. Also, heparin induces the loss of platelets and, paradoxically, can induce clotting in some patients (the "white clot" syndrome).

In order to achieve a catheter lock solution that is resistant to clotting and resistant to microbial infection, some have proposed the inclusion of antibiotics in heparin lock solutions or prophylactic systemic delivery of antibiotics to patients with CVDCs. However, because of frequent hospitalizations and receipt of antibiotics to treat bloodstream and vascular access infections, hemodialysis patients are at high risk for infection with drug-resistant bacteria. The rapid increase in vancomycin-resistant enterococci (VRE) in the United States has been attributed to use of antimicrobials, especially empirically prescribed vancomycin. Vancomycin is used commonly in dialysis patients for empiric therapy of symptoms of bloodstream infection because it can be administered once a week and is effective against two common pathogens, coagulase-negative Staphylococci and *Staphylococcus Aureus*. The greater the use of vancomycin, however, the greater the risk of inducing vancomycin-resistant *staphylococcus*, and if this is the cause of septicemia, there are then no effective drugs with which to treat these patients. Use of prophylactic vancomycin and other antibiotics to prevent catheter infection is therefore discouraged, and alternate means for fighting catheter infection are greatly needed.

Significant resources are currently being invested in a search for alternatives to heparin for catheter lock that do not have the above disadvantages, and for catheter formulations that have antimicrobial properties without including antibodies. For example, the present inventor has previously described catheter lock solutions including antimicrobial concentrations of citrate. Citrate provides effective anticoagulant properties when used in a catheter lock solution and, at a high concentration (i.e., at about 47% by weight), citrate also provides effective antimicrobial properties. One challenge presented by such a solution is that the high specific gravity of a concentrated citrate solution makes the solution tend to "run out" of a catheter over time. In addition, there are potential serious side effects if highly concentrated citrate is infused into a patient's bloodstream. These problems can be reduced by lowering the concentration of citrate in the solution, and even low concentrations of citrate have been shown to be at least equal to heparin in terms of maintaining catheter patency; however, lowering the concentration of citrate does result in a decrease in antimicrobial effects.

In light of the above-described problems, there is a continuing need for advancements in the field of catheter lock solutions. The present invention addresses this need and provides a wide variety of benefits and advantages.

SUMMARY

In one form, the invention provides an aqueous catheter lock solution comprising citrate and a paraben dispersed or dissolved therein. The citrate and the paraben preferably have concentrations effective to eliminate infection and to reduce the likelihood of subsequent infections. In alternative forms of the invention, the paraben is methyl paraben, propyl paraben, a combination of methyl paraben and propyl paraben, or any one of or a mixture of methyl paraben, ethyl paraben, propyl paraben and butyl paraben. When the term "butyl" is used herein, it is intended to refer to any of four isomeric monovalent radicals $C_4H_9$ derived from butanes. The citrate can advantageously be provided in the form of trisodium citrate dihydrate or other citrate salt. The relative density of the solution is selected in certain embodiments to be similar to the relative density of a patient's blood, and to thereby optimize the length of time that the solution remains in a catheter. The solution in other embodiments also includes a viscosifying agent and/or additional pharmaceutically acceptable materials. In one particularly preferred embodiment, a catheter lock solution is provided that includes citrate, a paraben and a photo-oxidant having antimicrobial effect. One photo-oxidant that has been shown by the inventors to have excellent antimicrobial properties is methylene blue.

In another form, the present invention provides a method for treating patients having an indwelling intravascular catheter. In one embodiment, the method comprises selecting a patient having an indwelling catheter defining a lumen therethrough; and infusing an aqueous catheter lock solution into the lumen, the solution comprising citrate and a paraben dispersed or dissolved therein. The invention is particularly useful in treating a patient having an infection or a substantial risk of infection related to the presence of the catheter.

In yet another form of the invention, there is provided an infusion device for infusing a lock solution into a lumen of a catheter. The device includes a syringe and a pharmaceutically acceptable lock solution contained within the syringe. The lock solution includes citrate and a paraben dispersed or dissolved therein. In a preferred embodiment, the syringe containing the lock solution is sterilized.

The invention also provides a method of treating animals having a surgically implanted catheter. The method includes infusing into the catheter a pharmaceutically acceptable lock solution comprising a bactericidal component that consists essentially of citrate and a paraben. In a preferred embodiment, the bactericidal component does not include an antibiotic.

In still another form, the invention provides devices, methods and compositions relating to the pretreatment of a catheter or other medical implant prior to use. In one embodiment, the catheter is soaked in a solution including a paraben for a period of time, and thereby impregnated with the paraben to provide a catheter featuring resistance to infection. Such soaking solutions preferably include the paraben at a high concentration. Due to the solubility limits of parabens in water, high concentrations of parabens can advantageously be provided by dissolving the paraben in alcohol or a water/alcohol mixture.

In another form, the present invention provides a kit for locking a patient's catheter. The kit includes a container having therein a catheter lock solution comprising citrate and a paraben dispersed or dissolved therein; and instructions, recorded in a medium, for infusing the solution into a lumen of an indwelling catheter.

Further objects, features, aspects, forms, advantages and benefits shall become apparent from the description and drawings contained herein.

While the actual nature of the invention covered herein can only be determined with reference to the claims appended hereto, certain forms and features, which are characteristic of the preferred embodiments disclosed herein, are described briefly as follows.

DETAILED DESCRIPTION OF THE PREFERRED EMBODIMENTS

For the purposes of promoting an understanding of the principles of the invention, reference will now be made to the embodiments described herein and specific language will be used to describe the same. It will nevertheless be understood that no limitation of the scope of the invention is thereby intended. Any alterations and further modifications in the described fluids, methods, devices or kits, and any further applications of the principles of the invention as described herein, are contemplated as would normally occur to one skilled in the art to which the invention relates.

In accordance with the invention, a catheter lock solution is used to provide anticoagulant and antibacterial properties to an implanted catheter as the lock solution resides in the catheter between uses. As used herein, the term "lock solution" refers to a solution that is injected or otherwise infused into a lumen of a catheter with the intention of allowing at least a portion of a lock solution to remain in the lumen until it is desired or required to access that particular lumen again, typically for additional treatment, i.e., infusion or withdrawal of fluid. It is desired that at least a portion the lock solution remain in the lumen for a desired amount of time lasting from about 1 hour to 3 or 4 days or longer. However, frequently the lock solution is changed on a daily basis during regular care and sterile maintenance of the indwelling catheter. Use of a lock solution in accordance with the present invention provides particular advantages for patients with catheters by inhibiting catheter-related infections and by preventing catheter occlusion.

A catheter used in connection with the present invention typically can either be an acute (temporary) or chronic (long-term) catheter surgically implanted in an animal. The catheter usually is inserted into a vein or artery. The catheter is typically used in varying intervals to administer fluids, nutrients, and medications into the body. The catheter also can be used to withdraw body fluids, such as blood for hemodialysis treatment. When not in use, the catheter remains in its position, commonly an intravascular position, until a subsequent treatment is performed.

The catheters that may be used in accordance with this invention include known and commonly used catheters and are readily available from a variety of commercial sources. The catheters may vary in configuration and size. One type of catheter commonly used in accordance with this invention is a tunneled catheter that includes a cuff for ingrowth of tissue to anchor the catheter. Examples of catheters that may be used include, but are not restricted to, an ASH SPLIT CATH and DUOSPLIT by Ash Access Technology, Inc. (Lafayette, Ind.) and Medcomp (Harleysville, Pa.); Tesio Catheters by Medcomp; PERM CATH by Quinton Instrument Company (Seattle, Wash.); and HICKMAN and VAS CATH by Bard, Inc. (Salt Lake City, Utah). Catheters containing totally subcutaneous ports are also useful in the present invention; examples include LIFESITE by Vasca (Topsfield, Me.); and DIALOCK by Biolink, Inc. of (Boston, Mass.). The catheters are manufactured to function for several months. For example, TESIO catheters can last for up to four years with proper intervention. However, in actual practice prior to the present invention, the catheters have exhibited limited longevity because of occlusion and/or infection. The catheters frequently must be removed and/or replaced upon the occurrence of occlusion and/or infection.

Figure 1:
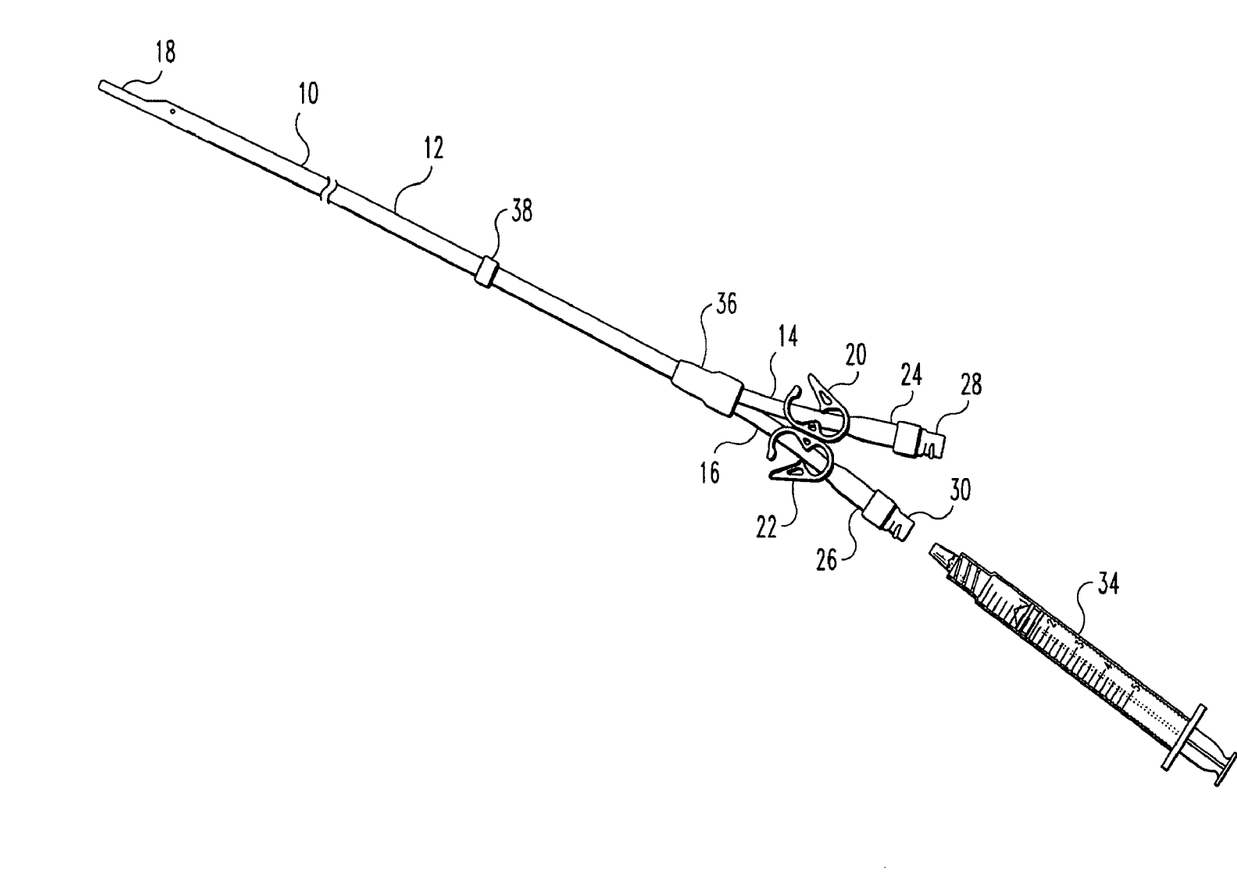
FIG. 1 is a perspective view of one embodiment of a catheter and syringe for infusing a lock solution into a catheter for use with the present invention.

FIG. 1 depicts one example of a catheter 10 for use with this invention. Catheter 10 is a dual lumen catheter and includes an outer sheath 12 having a cuff 38 and first and second lumens 14 and 16, respectively. Lumens 14 and 16 extend from distal tip 18 through sheath 12 and exit from sheath 12 at connection 36. Each of lumens 14 and 16 include releasable clamps 20 and 22, respectively. Each of lumens 14 and 16 terminate in a threaded end 24 and 26, which can be threadedly attached to protective end caps 28 and 30, respectively. Fluids including a lock solution can be infused or withdrawn from each lumen 14 and 16 by making a Luer connection between a syringe 34 and the ends 24 and 26 of catheter 10. Alternatively, fluids can be infused or withdrawn from each lumen by inserting a needle (not shown) through protective end caps 28 and/or 30 after protective end caps 28 and/or 30 have been sterilized by cleaning successively, for example with Betadine and alcohol. As yet another alternative, one or both protective end caps 28 and 30 can be removed and threaded ends 24 and 26 can be threadedly attached via a connector (not shown) to lines for infusion or withdrawal of fluids (not shown). Once a desired treatment session has been completed, the lumens are typically flushed with normal saline, after which a lock solution is injected into each lumen and fresh, sterile protective end caps are placed on the ends 24 and 26 of the catheter. All procedures are performed using standard sterile techniques well known to those skilled in the art. The catheters for use with this invention can be prepared from a variety of materials, including, for example, silicon, polyurethane, polyvinyl, silicone, or silastic elastomer.

In one form, the present invention provides a catheter lock solution including citrate and a paraben dispersed or dissolved therein. A person of ordinary skill in the art will readily understand that the term "paraben" is used to refer to an alkyl ester of p-hydroxybenzoic acid. In one embodiment, the paraben is selected from methyl paraben, ethyl paraben, propyl paraben, butyl paraben and a mixture of any two or more of said parabens. In another embodiment, the paraben is methyl paraben, propyl paraben or a mixture thereof. The citrate in one preferred embodiment is provided in the form of a citrate salt such as, for example, trisodium citrate dihydrate.

In one embodiment, the lock solution comprises citrate and methyl paraben. The amount of methyl paraben in the solution is limited only by the solubility limit of the methyl paraben in the aqueous citrate solution. In an exemplary citrate/methyl paraben catheter lock solution, the concentration of methyl paraben is from about 0.005 to about 0.5 percent. In another embodiment, the concentration of methyl paraben is from about 0.01 to about 0.5 percent. As used herein, the term "percent" or the symbol "%" is intended to refer to a concentration measured in grams per 100 milliliters of final solution.

In an alternative embodiment, the lock solution comprises citrate and propyl paraben. The amount of propyl paraben in the solution is limited only by the solubility limit of the propyl paraben in the aqueous citrate solution. In an exemplary citrate/propyl paraben catheter lock solution, the concentration of propyl paraben is from about 0.005 to about 0.5 percent. In another embodiment, the concentration of propyl paraben is from about 0.01 to about 0.2 percent.

In another preferred embodiment, the lock solution comprises citrate and a mixture of methyl paraben and propyl paraben. In an exemplary citrate/methyl paraben/propyl paraben catheter lock solution, the total concentration of the parabens is from about 0.05 to about 0.6 percent. In another embodiment, the total concentration of the parabens is from about 0.1 to about 0.3 percent. In yet another embodiment, the concentration of methyl paraben is from about 0.05 to about 0.5 percent and the concentration of propyl paraben is from about 0.005 to about 0.5 percent'. In still another embodiment, the concentration of methyl paraben is from about 0.05 to about 0.3 percent and the concentration of propyl paraben is from about 0.005 to about 0.3 percent. In a particular embodiment that has been found to have excellent properties, methyl paraben has a concentration of about 0.18 percent and propyl paraben has a concentration of about 0.02 percent in the fluid.

Although it is not intended that the present invention be limited by any theory whereby it achieves its advantageous results, it is believed that the citrate prevents coagulation by chelating the calcium in the adjacent blood. Decreasing the citrate concentration decreases the effect of calcium to catalyze numerous reactions that form blood clots. Citrate as an anticoagulant catheter lock is preferably present at a concentration at least as high as necessary to significantly decrease the ionized calcium concentration in blood, even when the lock solution is diluted by blood at the tip of a catheter. In one preferred embodiment, sodium citrate is present in a lock solution at a concentration of from about 1.5 to about 47 percent. In another embodiment, citrate is present at a concentration of from about 1.5 to about 23 percent. In yet another embodiment, citrate is present at a concentration of from about 1.5 to about 15 percent. In another embodiment, citrate is present at a concentration of up to about 20 percent.

The above concentrations are presented as "percent" of mostly trisodium citrate in water. When various combinations of salts of citrate are combined, such as trisodium citrate with citric acid, for example to obtain a certain pH, it is more accurate and helpful to express the concentration of citrate as a molar concentration, with a certain percentage of salts being sodium, hydrogen or other cations. Thus, in one embodiment, citrate is present at a concentration of at least about 0.004 Molar, more preferably from about 0.01 to about 1.0 Molar. Another embodiment includes citrate at a concentration of from about 0.1 to about 0.5 Molar. Yet another embodiment includes citrate at a concentration of about 0.24 Molar.

At a citrate concentration of 7% by weight, the citrate has a strong anticoagulant effect in the catheter lock solution. At this concentration, however, it is believed that citrate alone would not provide a significant antimicrobial property. The present invention relates to the discovery, which has been experimentally established that a mixture of citrate, methyl paraben and propyl paraben has unexpected and surprisingly effective antibacterial activity when used as a catheter lock solution in accordance with the present invention. In a series of tests with multiple microorganism, solutions including citrate, methyl paraben and propyl paraben dispersed or dissolved therein effectively killed all species of bacteria within 1 day (and most within one hour), while a solution including heparin and a paraben, a solution including saline and a paraben, a solution including only 7% citrate and a straight saline solution have little or no effect on the organisms.

Furthermore, the excellent antimicrobial effect exhibited by the citrate/paraben mixture has surprisingly been found to be independent of the pH of the solution. In this regard (and as shown in the Example below), a solution including 7% citrate by weight, 0.18% methyl paraben by weight and 0.02% propyl paraben by weight was shown to have substantially equal antimicrobial effect on a wide variety of bacterial species at a pH of about 4.5 and at a pH of about 6.2. Further information regarding experimental work involving these solutions is set forth in the Examples below. In a preferred embodiment of the invention, the pH of the inventive catheter lock solution is from about 4 to about 8.

In one preferred embodiment, an inventive catheter lock solution includes citrate (provided, for example, in the form of trisodium citrate dihydrate) at a concentration of about 7% and a paraben component having a concentration of about 0.2%. In one preferred embodiment about 90% of the paraben component is methyl paraben and about 10% of the paraben component is propyl paraben.

A problem that must be addressed with any catheter lock solution is that the solutions do not permanently stay within the catheter. Some of the catheter lock solution exits the end of the catheter during the infusion (often about ⅓ of the injected volume) when a volume is injected into the catheter equal to the lumen volume of the catheter. In addition, the portion remaining in the end of the catheter is typically washed out slowly by flow of blood through the side-holes of the catheter (if present). Other lock solution slowly diffuses from the body of the catheter through the end of the catheter during the time that lapses between dialysis treatments.

In the case of concentrated citrate, for example, gravitational effects also come into play. It is of course understood that the densities of citrate solutions increase as the concentrations of citrate therein increase. The relative density of 23% citrate, for example, is 1.120, which is significantly higher than the relative density of blood. Thus, when the patient is standing, the segment of the inner portion of the catheter in the vena cava is vertical. Gravitational force causes citrate at this concentration to slowly leave the catheter. In the laboratory, in some types of catheters positioned vertically (such as the double-D shaped Ash Split Cath catheters), 23% citrate lock can be shown to slowly exit from the distal part of the catheter over 3-5 days, into blood or blood substitute (with the same relative density). In other catheters (such as cylindrical Tesio catheters) the 23% citrate lock does not exit over time.

In vitro studies have indicated that the density of a lock solution is important in determining the length of time that the lock solution remains in the catheter. The relative density of blood with hematocrit of 32% is approximately 1.040. If a catheter lock solution with relative density higher than this is placed into a catheter positioned vertically, the lock solution will exit from the catheter at a slow rate. Increasing the viscosity with polymeric substances such as PEG slows but does not prevent the egress of the lock solution. Therefore, in certain embodiments of the invention, the citrate concentration in a lock solution is selected such that the density of the lock solution is sufficiently close to the density of the patient's blood that the solution does not exit the catheter during the lock period to an unacceptable degree.

It is believed that 7% sodium citrate (0.24 Molar citrate) alone is the concentration that matches a blood relative density of 1.040. This concentration of citrate does not have significant antibacterial effect at neutral or acid pH; however, the antithrombotic effect of 0.24 Molar citrate will remain very high even with some diffusion out of the catheter. Not only is the specific gravity of this solution at or near that of blood, thus minimizing or eliminating the "running out" of the solution from the end of a catheter, but is has also been shown to exhibit a surprisingly high antimicrobial effect when combined with a low concentration of parabens.

In one aspect of the invention, therefore, a catheter lock solution comprising citrate and a paraben is provided that has a density of from about 1.000 to about 1.300 g/ml. In another embodiment, a lock solution comprising citrate and a paraben has a density of from about 1.000 to about 1.080 g/ml. In still another embodiment, a lock solution comprising citrate and a paraben is provided having a density of from about 1.030 to about 1.050 g/ml. In yet another embodiment, an inventive lock solution comprising citrate and a paraben has a density of from about 1.035 to about 1.045 g/ml. It is understood that the density of a given patient's blood may differ from the density of the blood of another patient. Thus, the present invention also contemplates matching the relative density of a catheter lock solution to within a predetermined tolerance of the relative density of whole blood of a given patient (such as, for example, within 0.040 g/ml of the relative density of the patient's blood). Such density matching is within the purview of a person of ordinary skill in the art in view of the present description. Closely matching the densities has the advantageous effect of aiding in the retention of the catheter lock solution within the catheter between treatments. When the relative densities are relatively close, gravitational force does not tend to urge the catheter lock solution out of the catheter when the patient is upright. Similarly blood will not enter the catheter when the catheter is upward directed as in the femoral vein when the patient is standing (as can happen with a low-density catheter lock such as heparin).

In another aspect of the invention, the catheter lock solution may also include an agent to modify viscosity, as described in International Publication No. WO 00/10385, which is incorporated herein by reference in its entirety. The presence of a viscosifying agent is particularly useful, for example, when the relative density of a given catheter lock solution is not the same as the density of a patient's blood.

Therefore, in certain preferred embodiments, a lock solution is provided that comprises citrate, a paraben and one or more agents to adjust viscosity to help retain the lock within the catheter for a desired amount of time. It is well known that catheters are manufactured to have a variety of configurations and lumen diameters. For example, catheters can include single or double lumens. The double lumens can be fused adjacent to each other or they can be concentric. The lumens can have varying cross-sectional areas and shapes, ranging from substantially circular to substantially ovoid. As discussed above, a phenomenon common to most lock solutions is that a portion of the solution at the distal end of the lumen diffuses into the patient's blood stream and is replaced in the catheter by blood. The rate of diffusion of a lock solution from a lumen can be influenced not only by the density of the lock solution, but also by the cross-sectional shape and area of the particular lumen(s) and the viscosity of the lock solution. A lock solution of the present invention is preferably prepared to have a viscosity and density such that a substantial portion of the lock solution does not diffuse or flow out of a catheter lumen under normal circumstances within several days.

Viscosifying agents that can advantageously be selected for use in accordance with the present invention include those pharmaceutically acceptable agents known or commonly used in treatment of animals including humans. Examples include, but are not limited to, dextran, polyethylene glycol, glycerin, polygeline, and non-metabolizable sugars such as sorbitol and mannitol and mixtures of these compounds. Viscosifying agents that increase the viscosity of a lock solution allow a higher concentration of citrate to be used without having an unacceptable degree of egress of the lock solution from the catheter due to high density of the lock solution.

While it is understood that optimal viscosity and density are dependent upon the shape and size of a particular lumen, a person of ordinary skill in the art, in view of the description herein, can readily determine a desired density and viscosity for a particular catheter without undue experimentation. It is of course understood that the need for viscosifying agents is reduced or eliminated in a lock solution having a relatively lower concentration of citrate and a density closely matched to that of blood. The antiseptic effect of the citrate, which is reduced by the reduction in the citrate concentration, is achieved by the inclusion of a paraben or a mixture of parabens in an amount whereby the citrate and paraben together exhibit an antiseptic effect.

An inventive lock solution can be prepared to include a variety of other pharmaceutically acceptable agents. For example, the lock solution can include salts, such as, for example, sodium chloride or other sodium salts. The lock solution can also include a variety of other antibacterial, antimicrobial and anticoagulant agents. Such antibacterial and antimicrobial agents are well known to those skilled in the art and can include, without limitation, gentamicin, vancomycin, and mixtures of these agents. Additional anticoagulant agents that can be included in an inventive catheter lock solution include, for example, heparin, urokinase, tissue plasminogen activation (tPA) and mixtures of these agents. When the anticoagulant includes heparin, the heparin is preferably present at a concentration of from about 100 units/ml to about 10,000 units/ml.

By "pharmaceutically acceptable", it is meant that the lock solution and the included salts and other additives which are, within the scope of sound medical judgment, suitable for use in contact with tissues of humans and lower animals without undue toxicity, irritation, allergic response, and the like, and are commensurate with the reasonable benefit/risk ratio. It is also typically necessary that a composition be sterilized to reduce the risk of infection. For example, pharmaceutically acceptable salts are well-known in the art, and examples can be found in S. M. Berge et al. described in detail in J. Pharmaceutical Science, 66:1-19, 1977.

Another example of a pharmaceutically acceptable agent that can be included in a lock solution made or selected in accordance with the invention is a photo-oxidant, such as, for example, methylene blue. As used herein, the term "photo-oxidant" is defined to mean a photo-oxidant that has antimicrobial properties when present at a suitable concentration in an inventive solution. The use of methylene blue and other photo-oxidants in a catheter lock solution is discussed in U.S. Patent Application Publication No. US 2004/0092890, which is hereby incorporated herein by reference in its entirety. The present inventors have discovered that the inclusion of a photo-oxidant in a catheter lock solution along with citrate and a paraben results in enhanced antimicrobial properties. As such, in another excellent aspect of the present invention, there are provided catheter lock solutions that include citrate, a paraben and a photo-oxidant dissolved in the solution. In one preferred embodiment, the photo-oxidant is methylene blue. Alternative photo-oxidants that can be selected for use in accordance with the invention include, without limitation, Rose Bengal, hypericin, methylene violet, proflavine, riboflavin, rivanol, acriflavine, toluide blue, trypan blue, neutral red and mixtures thereof.

In one embodiment of the invention, the concentration of the photo-oxidant in the solution is up to about 1500 mg/100 ml. In another embodiment, the concentration of the photo-oxidant in the fluid is from about 1 to about 1500 mg/100 ml. In still another embodiment, the concentration of the photo-oxidant in the fluid is from about 1 to about 1000 mg/100 ml. In yet another embodiment, the concentration of the photo-oxidant in the fluid is from about 1 to about 100 mg/100 ml. In a further embodiment, the concentration of the photo-oxidant in the fluid is from about 1 to about 50 mg/100 ml. In another embodiment, the concentration of the photo-oxidant in the fluid is about 10 mg/100 ml.

In addition to enhancement of the antimicrobial properties of a catheter lock solution, a photo-oxidant is advantageous in that it imparts a color to the solution. The present application also contemplates the use of other coloring agents in catheter lock solutions made or used in accordance with the invention. Coloring agents can be used, for example, to provide a safety function, indicating to observers that the catheter contains a catheter lock solution. For example, methylene blue at a concentration of 10 mg/100 ml has a dark blue color in a syringe, and a noticeably blue color within the clear external segments of the catheter. Over time, the methylene blue solution lightly stains the inside of catheters made of polyurethane or silicone, but the injected lock solution still makes the segments noticeably darker in color. Therefore the presence of the lock solution is recognizable. In addition, it is possible to use a system of color coordination in which different coloring agents are used to identify, for example, different citrate concentrations, different paraben concentrations or mixtures, or perhaps lock solutions that include other additives, such as, for example, anticoagulants or antibiotics.

In addition to inventive catheter lock solutions, as described above, the present invention also provides methods of inhibiting infections in an animal having an indwelling intravascular catheter. In one aspect, therefore, the invention provides a method that includes selecting a patient having an indwelling catheter defining a lumen therethrough, and infusing an aqueous catheter lock solution into the lumen, the solution comprising citrate and a paraben dispersed or dissolved therein. In a preferred manner of practicing the invention, the method comprises infusing an amount of the lock solution that is from about 80% to about 120% of the internal volume of the catheter being locked.

Once a lock solution is infused into the lumen of a catheter in accordance with the invention, it is preferably allowed to remain until it is time to access that particular catheter or lumen again. It is desirable to remove the catheter lock before starting the dialysis procedure or using the catheter for fluid infusion, especially if the catheter lock solution includes heparin.

In other aspects of the invention, the catheter lock solution containing citrate and a paraben may be injected into catheters used for access to other body spaces besides veins or arteries. For example, catheters used in peritoneal dialysis access the peritoneum (the space defined by the peritoneal membrane and exterior to the organs in the abdomen). These catheters also have a risk of bacterial and fungal contamination. After draining and infusing peritoneal dialysate solutions, a lock solution including citrate and a paraben is infused into the catheter. Other catheters with risk of infection include catheters in the urinary bladder, the cerebral spinal fluid (around the central nervous system) and the subcutaneous space (under the skin).

The present invention also contemplates the pretreatment of a catheter to provide an infection-resistant catheter. In an advantageous aspect of the invention, therefore, a catheter selected for implantation into a patient, such as, for example, into a vascular site of a patient, can be pretreated with a solution including a paraben to coat and impregnate the catheter surfaces with the paraben, thereby providing an infection-resistant catheter. Generally, it is sufficient to soak the catheter in an excess volume of an aqueous paraben solution, followed by washing in water or in a solution mimicking physiological conditions of use to remove non-absorbed material. In a preferred embodiment, however, it is desirable to soak the catheter in a high concentration of paraben that exceeds the solubility limits of the paraben in water. In one preferred embodiment, the paraben is dissolved in alcohol or a water/alcohol mixture, and the catheter is soaked therein. The catheter, pretreated in this manner, has an increased resistance to infection when it is placed into position, particularly when a solution comprising citrate or a solution comprising citrate and a paraben is placed therein.

It is also contemplated that a wide variety of other polymeric medical devices can be treated as described above. For example, medical devices that are amenable to coating and impregnation by a paraben solution include non-metallic materials such as thermoplastic or polymeric materials. Examples of such materials are rubber, plastic, polyethylene, polyurethane, silicone, Gortex (polytetrafluoroethylene), Dacron (polyethylene tetraphthalate), Teflon (polytetrafluoroethylene), latex, elastomers and Dacron sealed with gelatin, collagen or albumin. Devices especially suited for application of the antimicrobial combinations of this invention include, for example, peripherally insertable central venous catheters, dialysis catheters, long term tunneled central venous catheters, peripheral venous catheters, short-term central venous catheters, arterial catheters, pulmonary artery Swan-Ganz catheters, urinary catheters, long term urinary devices, tissue bonding urinary devices, vascular grafts, vascular catheter ports, wound drain tubes, hydrocephalus shunts, peritoneal catheters, pacemaker capsules, small or temporary joint replacements, urinary dilators, heart valves and the like.

One embodiment of the present invention, therefore, is a method for impregnating a non-metallic medical implant with a paraben comprising the steps of forming an aqueous solution of an effective concentration of a paraben to inhibit the growth of bacterial and fungal organisms; and applying the solution to at least a portion of a medical implant under conditions where the paraben permeate the material of the medical implant. The paraben solution can have a wide variety of concentrations, depending upon the amount of paraben one desires to become impregnated in the catheter or other device. In addition, the amount of time that the catheter or other device is soaked in the solution can be varied to vary the degree of impregnation. Typically it will be desired to soak the catheter for at least about an hour, and often significantly longer.

After the impregnated implant is removed from the solution, and optionally allowed to dry, the implant is preferably rinsed with a liquid to remove excess paraben from the surface thereof. It is of course understood that the invention can be used in certain embodiments to pre-treat a portion of a catheter or other device. In the case of an intravascular catheter, for example, it may be desirable to pre-treat only the lumen of the catheter. This can be done by simply placing a pretreatment solution into the lumen of the catheter rather than soaking the entire catheter. Alternatively, it is possible to pre-treat only a portion of a catheter that will reside within a patient's artery or vein, or to pre-treat only the portion that lies transcutaneously.

In another aspect, the invention involves an infusion device for infusing a lock solution into a lumen of a catheter. The infusion device includes a syringe and a pharmaceutically acceptable lock solution contained within the syringe, the lock solution including citrate and a paraben dispersed or dissolved therein. In a preferred embodiment, the syringe containing the lock solution is sterilized. The syringe can be advantageously used to infuse a catheter lock solution into a catheter that has an injection port affixed thereto by attaching a needle to the syringe and injecting the needle into the port. Alternatively the syringe can be used by uncapping a catheter and attaching the syringe directly to the catheter.

In another aspect of the invention, there is provided a catheter lock kit. In one preferred embodiment, a kit includes a container having therein a catheter lock solution, the catheter lock solution comprising citrate and a paraben dispersed or dissolved therein; and instructions, recorded in a medium, for infusing the solution into a lumen of an indwelling catheter.

As will be appreciated by those of ordinary skill in the art, in one form of the invention there has been described an aqueous catheter lock solution comprising citrate and a paraben dispersed or dissolved therein. The citrate and the paraben preferably have concentrations effective to eliminate infection and to reduce the likelihood of subsequent infections. The solution can include, for example and without limitation, a member selected from the group consisting of methyl paraben, ethyl paraben, propyl paraben, butyl paraben and mixtures of any two or more of these.

In one embodiment of the invention, the solution comprises methyl paraben. In a preferred embodiment described herein, the concentration of methyl paraben in the solution is from about 0.005 to about 0.5 percent. In another embodiment, the solution comprises propyl paraben. In a preferred embodiment, the concentration of propyl paraben in the solution is from about 0.005 to about 0.5 percent. In yet another embodiment, the solution comprises a mixture of methyl paraben and propyl paraben. In a preferred embodiment, the concentration of methyl paraben in the solution is from about 0.05 to about 0.5 percent and the concentration of propyl paraben in the solution is from about 0.005 to about 0.5 percent. In another preferred embodiment described herein, the concentration of methyl paraben in the solution is about 0.18% by weight and the concentration of propyl paraben in the solution is about 0.02% by weight.

The concentration of citrate in the solution is preferably at least as high as the calcium concentration in a patient's blood. In one preferred embodiment, the concentration of citrate in the solution is from about 1.5 to about 47% by weight. In another preferred embodiment, the concentration of citrate in the solution is from about 1.5 to about 23% by weight. In still another preferred embodiment, the concentration of citrate in the solution is from about 1.5 to about 15% by weight. In yet another preferred embodiment, the concentration of citrate in the solution is about 7% by weight.

In one catheter lock solution described herein, the citrate has a concentration of from about 1.5 to about 15 percent and the paraben has a concentration of from about 0.005 to about 0.6 percent. In another catheter lock solution, the concentration of citrate in the solution is from about 1.5 to about 15% by weight and the paraben concentration in the solution is from about 0.05 to about 0.3 percent. In yet another catheter lock solution, the concentration of citrate in the solution is about 7% by weight and the concentration of paraben in the solution is about 0.2% by weight.

In certain preferred embodiments, the citrate is provided in the solution in the form of a citrate salt. In one preferred embodiment, the citrate is provided in the solution in the form of trisodium citrate dihydrate.

In certain preferred embodiments described herein, a catheter lock solution is provided in which the pH of the solution is from about 4 to about 8. In other preferred embodiments, the relative density of the solution is from about 1.000 to about 1.300 g/ml. In another embodiment, the relative density of the solution is from about 1.000 to about 1.080 g/ml.

In other preferred embodiments, catheter lock solutions are described that further include a viscosifying agent. The viscosifying agent can be, for example, a member selected from the group consisting of dextran, polyethylene glycol, glycerin, polygeline, non-metabolizable sugars such as sorbitol and mannitol, and mixtures of these compounds.

In yet another form of the invention, there is described a catheter lock solution that includes citrate and a paraben dispersed or dissolved therein, and also includes a photo-oxidant dissolved in the solution. The photo-oxidant can be, for example and without limitation, a member selected from the group consisting of methylene blue, Rose Bengal, hypericin, methylene violet, proflavine, riboflavin, rivanol, acriflavine, toluide blue, trypan blue, neutral red and mixtures thereof. In a preferred embodiment of the invention, the photo-oxidant comprises methylene blue.

In one embodiment described herein, the concentration of methylene blue or other photo-oxidant in the solution is up to about 1500 mg/100 ml. In another embodiment, the concentration of the methylene blue or other photo-oxidant in the fluid is from about 1 to about 1500 mg/100 ml. In still another embodiment, the concentration of the methylene blue or other photo-oxidant in the fluid is from about 1 to about 1000 mg/100 ml. In yet another embodiment, the concentration of the methylene blue or other photo-oxidant in the fluid is from about 1 to about 100 mg/100 ml. In a further embodiment, the concentration of the methylene blue or other photo-oxidant in the fluid is from about 1 to about 50 mg/100 ml. In another embodiment, the concentration of the methylene blue or other photo-oxidant in the fluid is about 10 mg/100 ml.

In another aspect of the invention, there is described a method for treating a patient that includes: (1) selecting a patient having an indwelling catheter defining a lumen therethrough; and (2) infusing into the lumen an aqueous catheter lock solution made or selected in accordance with the present invention. In one manner of practicing this inventive method, the catheter is selected from the group consisting of an intravascular catheter and a body cavity catheter. In a preferred embodiment, the lumen of the catheter has an internal volume and said infusing includes infusing an amount of the lock solution that is from about 80% to about 120% of the internal volume.

In yet another aspect, the invention provides an infusion device for infusing a lock solution into a lumen of a catheter. The device includes a syringe; and a pharmaceutically acceptable lock solution contained within the syringe. The lock solution can be any one of a wide variety of lock solutions provided in accordance with the present invention, in all of its various aspects and embodiments described herein. In one preferred embodiment, the syringe containing the lock solution is sterilized.

In still another aspect of the invention, there is described a kit for locking a patient's catheter. The kit includes (1) a container having therein a catheter lock solution; and (2) instructions, recorded in a medium, for infusing the solution into a lumen of an indwelling catheter. The lock solution is one of a wide variety of lock solutions provided in accordance with the present invention, in all of its various aspects and embodiments described herein. In one preferred embodiment, the catheter is selected from the group consisting of an intravascular catheter and a body cavity catheter. In another preferred embodiment, the lumen of the catheter has an internal volume and instructions include instructions to infuse an amount of the lock solution of from about 80% to about 120% of the internal volume.

In a further aspect, the invention provides a method of treating animals having a surgically implanted catheter. The method includes infusing into said catheter a pharmaceutically acceptable lock solution comprising a bactericidal component, wherein the bactericidal component consists essentially of citrate and a paraben. In one embodiment, the bactericidal component consists essentially of citrate, a paraben and a photo-oxidant. In another embodiment, the bactericidal component does not include an antibiotic.

The invention will be further described with reference to the following specific Examples. It will be understood that these Examples are intended to be illustrative and not restrictive in nature.

EXAMPLE 1

A catheter lock solution was prepared in accordance with the invention to include citrate at a concentration of 7%, by weight (provided as trisodium citrate), methyl paraben at a concentration of 0.18%, by weight and propyl paraben at a concentration of 0.02% by weight. The target pH of the catheter lock solution was 4.5, and the actual pH of the solution during the test was measured at 4.58. This solution was put into contact with colonies of multiple species of bacteria by injection of bacteria spores into the prepared solution, and the bacteria was scored periodically (at 60 minutes, 24 hours, 48 hours and 72 hours) to determine the number of colony forming units (CFU) per milliliter. The data is set forth below in Table I:

TABLE I

| Test Microorganism | Recovery Level (CFU/ml) | | | | |
|---|---|---|---|---|---|
| | 0 Time | 60 min. | 24 hours | 48 hours | 72 hours |
| S. aureus ATCC 33591 | 500,000 | <100 | <100 | <100 | <100 |
| E. coli ATCC 35218 | 650,000 | <100 | <100 | <100 | <100 |
| E. coli ATCC 25922 | 460,000 | <100 | <100 | <100 | <100 |
| P. aeruginosa ATCC 27853 | 290,000 | <100 | <100 | <100 | <100 |
| C. alibicans ATCC 10231 | 560,000 | 290,000 | <100 | <100 | <100 |
| E. faecalis ATCC 376 | 610,000 | <100 | <100 | <100 | <100 |
| S. epidermidis ATCC 12228 | 440,000 | <100 | <100 | <100 | <100 |

EXAMPLE 2

A catheter lock solution was prepared in accordance with the invention to include citrate at a concentration of 7%, by weight (provided as trisodium citrate), methyl paraben at a concentration of 0.18%, by weight and propyl paraben at a concentration of 0.02% by weight. The target pH of the catheter lock solution was 6.2, and the actual pH of the solution during the test was measured at 6.26. This solution was put into contact with colonies of multiple species of bacteria by injection of bacteria spores into the prepared solution, and the bacteria was scored periodically (at 60 minutes, 24 hours, 48 hours and 72 hours) to determine the number of colony forming units (CFU) per milliliter. The data is set forth below in Table II:

TABLE II

| Test Microorganism | Recovery Level (CFU/ml) | | | | |
|---|---|---|---|---|---|
| | 0 Time | 60 min. | 24 hours | 48 hours | 72 hours |
| S. aureus ATCC 33591 | 500,000 | 5,900 | <100 | <100 | <100 |
| E. coli ATCC 35218 | 650,000 | <100 | <100 | <100 | <100 |
| E. coli ATCC 25922 | 460,000 | <100 | <100 | <100 | <100 |
| P. aeruginosa ATCC 27853 | 290,000 | <100 | <100 | <100 | <100 |
| C. alibicans ATCC 10231 | 560,000 | 300,000 | <100 | <100 | <100 |
| E. faecalis ATCC 376 | 610,000 | 100 | <100 | <100 | <100 |
| S. epidermidis ATCC 12228 | 440,000 | 100 | <100 | <100 | <100 |

EXAMPLE 3

Comparative Example

A catheter lock solution was prepared to include heparin with preservatives at a concentration of 2,500 units/ml. This lock solution was prepared by combining 1 ml of 5,000 unit/ml heparin, 1.5 mg/ml methyl paraben and 0.15 mg/ml propyl paraben with 1 ml 0.9% sterile saline. This solution was put into contact with colonies of multiple species of bacteria by injection of bacteria spores into the prepared solution, and the bacteria was scored periodically (at 60 minutes, 24 hours, 48 hours and 72 hours) to determine the number of colony forming units (CFU) per milliliter. The data is set forth below in Table III:

TABLE III

| Test Microorganism | Recovery Level (CFU/ml) | | | | |
|---|---|---|---|---|---|
| | 0 Time | 60 min. | 24 hours | 48 hours | 72 hours |
| S. aureus ATCC 33591 | 500,000 | 550,000 | 530,000 | >3,000,000 | >3,000,000 |
| E. coli ATCC 35218 | 650,000 | 610,000 | 450,000 | 196,000 | 106,000 |
| E. coli ATCC 25922 | 460,000 | 420,000 | 130,000 | 166,000 | 116,000 |
| P. aeruginosa ATCC 27853 | 290,000 | 310,000 | 14,800 | 700 | 200 |
| C. alibicans ATCC 10231 | 560,000 | 380,000 | 550,000 | 270,000 | 360,000 |
| E. faecalis ATCC 376 | 610,000 | 640,000 | 60,000 | 1,370,000 | 1,710,000 |
| S. epidermidis ATCC 12228 | 440,000 | 390,000 | 113,000 | 44,000 | 9,500 |

EXAMPLE 4

Comparative Example

A saline-only (0.85%) catheter lock solution was prepared. The saline solution was put into contact with colonies of multiple species of bacteria by injection of bacteria spores into the prepared solution, and the bacteria was scored periodically (at 60 minutes, 24 hours, 48 hours and 72 hours) to determine the number of colony forming units (CFU) per milliliter. The data is set forth below in Table IV:

TABLE IV

| Test Microorganism | Recovery Level (CFU/ml) | | | | |
|---|---|---|---|---|---|
| | 0 Time | 60 min. | 24 hours | 48 hours | 72 hours |
| S. aureus ATCC 33591 | 500,000 | 820,000 | >3,000,000 | >3,000,000 | >3,000,000 |
| E. coli ATCC 35218 | 650,000 | 620,000 | >3,000,000 | >3,000,000 | >3,000,000 |
| E. coli ATCC 25922 | 460,000 | 780,000 | >3,000,000 | >3,000,000 | >3,000,000 |
| P. aeruginosa ATCC 27853 | 290,000 | 189,000 | >3,000,000 | >3,000,000 | >3,000,000 |
| C. alibicans ATCC 10231 | 560,000 | 550,000 | 234,000 | 340,000 | 430,000 |
| E. faecalis ATCC 376 | 610,000 | 700,000 | >3,000,000 | >3,000,000 | >3,000,000 |
| S. epidermidis ATCC 12228 | 440,000 | 570,000 | 80,000 | 7,800 | 5,900 |

EXAMPLE 5

Comparative Example

A catheter lock solution was prepared to include methyl paraben at a concentration of 0.09%, by weight and propyl paraben at a concentration of 0.01% by weight (in saline, without citrate). This solution was put into contact with colonies of multiple species of bacteria by injection of bacteria spores into the prepared solution, and the bacteria was scored periodically (at 60 minutes, 24 hours, 48 hours and 72 hours) to determine the number of colony forming units (CFU) per milliliter. Based upon periodic visual inspections of the samples over a period of 72 hours, the paraben-only catheter lock solution was observed to have no significant antibacterial effect on the growth of colonies of S. aureus (ATCC 33591); E. coli (ATCC 35218); E. coli (ATCC 25922); P. aeruginosa (ATCC 27853); C. alibicans (ATCC 10231); and E. faecalis (ATCC 376). The paraben-only solution did have an antibacterial effect upon S. epidermidis (ATCC 12228), upon which the solution had a significant antibacterial effect within the first 24-hour period.

EXAMPLE 6

Two catheter lock solutions were prepared in accordance with the invention. The first included citrate at a concentration of 7%, by weight (provided as trisodium citrate), methyl paraben at a concentration of 0.18%, by weight, propyl paraben at a concentration of 0.02% by weight. The second included the same citrate at a concentration of 7%, by weight (provided as trisodium citrate), methyl paraben at a concentration of 0.18%, by weight, propyl paraben at a concentration of 0.02% by weight, plus methylene blue at a concentration of 0.01% by weight. The target pH of both catheter lock solutions was 6.2, and the actual pH of the solutions during the test was measured at 6.2. These solutions were put into contact with colonies of E. faecalis bacteria by injection of bacteria spores into the prepared solution, and the bacteria was scored periodically (at 0 minutes, 10 minutes, 20 minutes, 40 minutes and 60 minutes) to determine the number of colony forming units (CFU) per milliliter. The data is set forth below in Table V:

TABLE V

| Microorganism/ Lock Solution | Recovery Level (CFU/ml) | | | | |
|---|---|---|---|---|---|
| | 0 Time | 10 min. | 20 min. | 40 min. | 60 min. |
| E. faecalis Parabens only | 13,130,000 | 4,500,000 | 16,700,000 | 6,350,000 | 235,000 |
| E. faecalis Parabens plus methylene blue | 1,300,000 | 64,000 | <100 | <100 | <100 |

EXAMPLE 7

Two catheter lock solutions were prepared in accordance with the invention. The first included citrate at a concentration of 7%, by weight (provided as trisodium citrate), methyl paraben at a concentration of 0.045%, by weight, propyl paraben at a concentration of 0.005% by weight. The second included the same citrate at a concentration of 7%, by weight (provided as trisodium citrate), methyl paraben at a concentration of 0.045%, by weight, propyl paraben at a concentration of 0.005% by weight, plus methylene blue at a concentration of 0.015% by weight. The target pH of both catheter lock solutions was 6.2, and the actual pH of the solutions during the test was measured at 6.2. These solutions were put into contact with colonies of E. faecalis bacteria by injection of bacteria spores into the prepared solution, and the bacteria was scored periodically (at 0 minutes, 1 hour, 24 hours, 48 hours and 72 hours) to determine the number of colony forming units (CFU) per milliliter. The data is set forth below in Table V:

TABLE VI

| Microorganism/ Lock Solution | Recovery Level (CFU/ml) | | | | |
|---|---|---|---|---|---|
| | 0 Time | 1 hr. | 24 hr. | 48 hr. | 72 hr. |
| E. faecalis Parabens only | 26,180,000 | 2,845,000 | 2,800 | 213 | <100 |
| E. faecalis Parabens plus methylene blue | 12,100,000 | 332 | <100 | <100 | <100 |

EXAMPLE 8

Manufacturing of a Representative Catheter Lock Solution

Method

A catheter lock solution is formulated as a sterile mixture of USP grade chemicals in the following concentrations: 7% citrate solution by weight, 0.18% methyl paraben by weight and 0.02% propyl paraben. The solution is designed to have a relative density of 1.035 to 1.045, and pH of about 6.2. The citrate solution is prepared at the desired pH (6.2) by mixing 428 ml of 0.24 M trisodium citrate dihydrate solution (70.58 g/L) and 72 ml of 0.24 M anhydrous citric acid solution (46.10 g/L). The final solution is obtained by adding 0.18 g of methyl paraben and 0.02 g of propyl paraben per 100 ml of citrate solution in the actual batch size. The solution is stored at room temperature.

The bulk solution is then pumped into an aseptic filling area, passing through a secondary and then primary 0.2 micron sterilizing filter before flowing into a sterilized surge type or pressure type vessel. The sterilized solution in the sterile vessel flows to the filler where light resistant, type 1 glass vials (5 mL, Kimble, type 1 Borosilicate Glass Amber Vial, 13-mm Finish, Untreated) are conveyed and filled with the predetermined fill volume. The filled vials are then conveyed to the stoppering location where stoppers (West, 13 mm, 4432/50 Rubber Stopper) are placed in the vials. The vials are then conveyed to a capping machine which applies aluminum crimp seals with flip off caps to each vial (West, 13 mm Aluminum Seal, Flip-off Button). Overseals (crimped caps) are applied in a capping area outside of the aseptic processing area.

The filled, stoppered and capped vials are then inspected for visible particulate matter and other defects.

The starting materials for making the solution of this embodiment are readily available commercially.

EXAMPLE 9

Using an Inventive Catheter Lock Solution

At the end of a patient's hemodialysis treatment each lumen of the catheter is filled with the lock solution in an amount equal to the fill volume of the catheter lumen. Each lumen is filled to the tip using a quick bolus technique for the first ⅔ of the injected volume, and slow infusion (over 10 seconds) for the last ⅓ of the injected volume.

The catheter lock solution is removed before each dialysis procedure, by attaching a syringe to each catheter lumen and removing 1 mL more than the catheter lumen volume (about 3 mL total), discarding the syringe, then flushing the catheter with 5 mL of sterile normal saline.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An aqueous antimicrobial solution comprising about 1.5 to 47% by weight citrate, up to 1500 mg/100 ml methylene blue, and about 0.005-0.6 percent (g/100 ml) paraben dispersed or dissolved therein.

2. The solution of claim 1, wherein the paraben is methyl paraben, ethyl paraben, propyl paraben, butyl paraben, or a combination thereof.

3. The solution of claim 1, wherein the solution comprises methyl paraben.

4. The solution of claim 1, wherein the solution comprises propyl paraben.

5. The solution of claim 1, wherein the solution comprises methyl paraben and propyl paraben.

6. The solution of claim 5, wherein the concentration of methyl paraben in the solution is from about 0.05 to about 0.5 percent, and the concentration of propyl paraben in the solution is from about 0.005 to about 0.5 percent.

7. The solution of claim 1, wherein the concentration of citrate in the solution is at least as high as the calcium concentration in a patient's blood.

8. The solution of claim 1, wherein the concentration of citrate in the solution is from about 1.5 to about 23% by weight.

9. The solution of claim 1, wherein the citrate has a concentration of from about 1.5 to about 15% by weight.

10. The solution of claim 1, wherein the citrate is trisodium citrate dihydrate.

11. The solution of claim 1, wherein the pH of the solution is from about 4 to about 8.

12. The solution of claim 1, wherein the relative density of the solution is from about 1.000 to about 1.300 g/ml.

13. The solution of claim 1, wherein the solution further comprises a viscosifying agent.

14. The solution of claim 13, wherein the viscosifying agent comprises dextran, polyethylene glycol, glycerin, polygeline, a non-metabolizable sugar, or a combination thereof.

15. The solution of claim 1, wherein the citrate has a concentration of from about 1.5 to about 15% by weight, the concentration of methylene blue in the solution is up to about 1500 mg/100 ml, and the solution comprises about 0.05 to about 0.5 percent methyl paraben and about 0.005 to about 0.5 percent propyl paraben.

16. The solution of claim 1, further comprising alcohol.

17. The solution of claim 1, wherein the methylene blue has a concentration of about 1 mg/100 ml to about 100 mg/100 ml.

18. The solution of claim 1, wherein the paraben has a concentration of about 0.1 percent to about 0.3 percent.

19. The solution of claim 1, wherein the citrate has a concentration of from about 1.5 to about 23% by weight, the concentration of methylene blue in the solution is about 1 mg/100 ml to about 100 mg/100 ml, and the concentration of paraben is about 0.1 percent to about 0.3 percent.

20. An aqueous antimicrobial solution comprising about 0.01-1 M citrate, up to 1500 mg/100 ml methylene blue, and about 0.005-0.6 percent (g/100 ml) paraben dispersed or dissolved therein.

21. The solution of claim 20, wherein the concentration of citrate is about 0.1 to about 0.5 M.

22. The solution of claim 20, wherein the methylene blue has a concentration of about 1 mg/100 ml to about 100 mg/100 ml.

23. The solution of claim 20, wherein the paraben has a concentration of about 0.1% to about 0.3% by weight.

24. The solution of claim 22, wherein the paraben has a concentration of about 0.1% to about 0.3% by weight.

* * * * *